US00PP08493P

United States Patent [19]

Meilland

[11] Patent Number: Plant 8,493

[45] Date of Patent: Dec. 14, 1993

[54] MINIATURE ROSE PLANT NAMED 'MEICUPAG'

[75] Inventor: Alain A. Meilland, Antibes, France

[73] Assignee: The Conard-Pyle Company, West Grove, Pa.

[21] Appl. No.: 971,604

[22] Filed: Oct. 30, 1992

[51] Int. Cl.[5] ..... A01H 5/00

[52] U.S. Cl. ..... Plt./8.2

[58] Field of Search ..... Plt./8.2

[56] References Cited

U.S. PATENT DOCUMENTS

P.P. 7,136 2/1990 Laver ..... Plt. 8.2

*Primary Examiner*—Howard J. Locker

*Attorney, Agent, or Firm*—Burns, Doane, Swecker & Mathis

[57] ABSTRACT

A new and distinct variety of rose plant of the Miniature Class is provided which abundantly and continuously forms attractive long-lasting double aureolin yellow blossoms wherein the coloration is fairly stable. The plant is very bushy and upright, and forms strong glossy dark green vegetation. The blossoms are very slightly fragrant. The plant is well adapted to greenhouse forcing while grown in small containers, and is particularly well suited for use as a flowering pot plant when grown indoors or outdoors. Additionally, the plant is not particularly affected by cryptogamic diseases.

1 Drawing Sheet

SUMMARY OF THE INVENTION

The new variety of miniature rose plant was created by artificial pollination wherein two parents were crossed which previously had been studied in the hope that they would contribute the desired characteristics. The female parent (i.e., the seed parent) was the product of the pollination of the Rise 'N Shine variety (U.S. Plant Pat. No. 4,231) by the Savamark variety (nonpatented in the United States). The male parent (i.e., the pollen parent) of the new variety was the MEITRISICAL variety (nonpatented in the United States). The parentage of the new variety can be summarized as follows:

(Rise 'N Shine × Savamark) × Meitrisical.

The seeds resulting from the above pollination were sown and 12 plantlets were obtained which were physically and biologically different from each other. Selective study resulted in the identification of a single plant of the new variety.

It was found that the new variety of miniature rose plant of the present invention possesses the following combination of characteristics:

(a) forms in abundance on a continuous basis attractive double long-lasting blossoms which are of a fairly stable aureolin yellow coloration,
(b) forms dark green glossy foliage,
(c) exhibits a very bushy and upright growth habit,
(d) is very quick to cycle,
(e) exhibits excellent garden performance and is well adapted to greenhouse forcing when grown in a container, and
(f) is not particularly affected by cryptogamic diseases.

The new variety well meets the needs of the horticultural industry. It is particularly well-suited for use as attractive ornamentation as a flowering pot plant when grown indoors or outdoors. For instance, the new variety grows well in containers.

The new variety has been found to undergo asexual propagation in France by a number of routes, including budding, grafting, cuttage, etc. The characteristics of the new variety have been found to be strictly transmissible by such asexual propagation from one generation to another.

The new variety has been named the Meicupag variety.

BRIEF DESCRIPTION OF THE PHOTOGRAPH

The accompanying photograph shows as nearly true as it is reasonably possible to make the same, in a color illustration of this character, typical specimens of the plant parts of the new variety. The rose plants of the new variety described herein were eighteen months of age and were observed during April while growing on their own roots outdoors at LeCannet des Maures, Var, France.

DETAILED DESCRIPTION

Figures 1, 2, 3, 4, 5, 6, 7, 8, 9, 10, 11, 12, 13, 14, 15, 16:
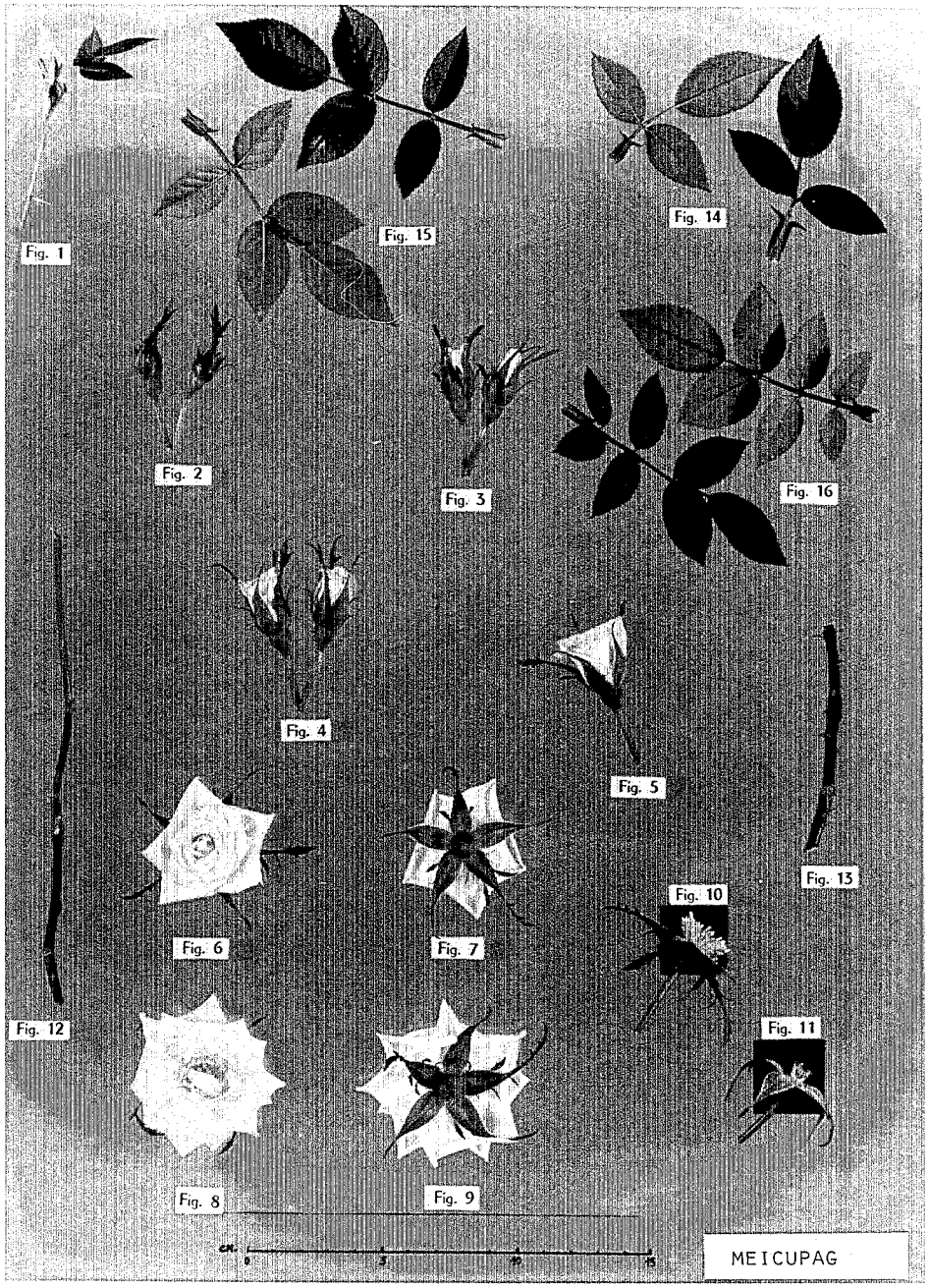
FIG. 1 illustrates a specimen of a young shoot.
FIG. 2 illustrates specimens of two floral buds before the opening of the sepals.
FIG. 3 illustrates specimens of two floral buds at the opening of the sepals.
FIG. 4 illustrates specimens of two floral buds at the opening of the petals.
FIG. 5 illustrates a specimen of a flower during the course of opening.
FIG. 6 illustrates a specimen of an open flower — plan view — obverse.
FIG. 7 illustrates a specimen of an open flower — plan view — reverse.
FIG. 8 illustrates a specimen of a fully open flower — plan view — obverse.
FIG. 9 illustrates a specimen of a fully open flower — plan view — reverse.
FIG. 10 illustrates a specimen of a floral receptacle showing the arrangement of the stamens and pistils.
FIG. 11 illustrates a specimen of a floral receptacle showing the arrangement of the pistils (stamens removed)
FIG. 12 illustrates a specimen of a flowering stem.
FIG. 13 illustrates a specimen of a main branch.
FIG. 14 illustrates specimens of leaves with three leaflets with the upper surface being shown at the right and the under surface being shown at the left.
FIG. 15 illustrates specimens of leaves with five leaflets with the upper surface being shown at the top and the under surface being shown at the bottom.
FIG. 16 illustrates specimens of leaves with seven leaflets with the under surface being shown at the top and the upper surface being shown at the bottom.

The chart used in the identification of the colors is that of The Royal Horticultural Society (R.H.S. Colour Chart). The terminology which precedes reference to the chart has been added to indicate the corresponding colors in common terms. The description is based on eighteen month old specimens of the new variety which were observed during April while growing on their own roots outdoors at LeCannet des Maures, Var, France.

Class: Miniature.

Plant:

*Height.*—Approximately 30 to 35 cm. on average when grown outdoors or in a one-gallon container on its own roots.

*Habit.*—Very bushy and upright.

Branches:

*Color.*—Young stems: light green, Yellow-Green Group 144B. Adult wood: medium green, Green Group 137B.

*Thorns.*—Size: small. Quantity: fairly numerous. Color: Yellow-Green Group 144B on young stems and Green Group 137B on mature wood.

Leaves:

*Petioles.*—Upper surface: striped, reddish brown on young foliage and medium green on mature foliage with glandular edges. Under surface: medium green with numerous prickles.

*Stipules.*—Adnate, pectinate, wide and linear.

*Leaflets.*—Number: 3, 5 (most often), and 7. Shape: spear-shaped. Serration: single and regular. Texture: very consistent. General appearance: dense, dark, and very glossy foliage. Color (young foliage): Upper surface: medium green, Green Group 143A. Under surface: light green, Green Group 143C. Color (adult foliage): Upper surface: dark green, Green Group 137A. Under surface: light green, Green Group 137C.

Inflorescence:

*Number of flowers.*—Approximately 1 to 7 per stem.

*Peduncle.*—Smooth, light green, straight and rigid, its length is approximately 3.5 cm. on average.

*Sepals.*—Upper surface: tomentose and greenish in coloration. Under surface: medium green, smooth, with edges which are more or less glandular and appendiculated.

*Buds.*—Shape: egg-shaped. Length: approximately 2 cm. on average. Size: medium. Color upon opening: Upper surface: aureolin, Yellow Group 12A, and sometimes slightly edged with maize yellow, Yellow-Orange Group 21B. Under surface: aureolin, Yellow Group 12A, and sometimes slightly edged with Indian orange, Orange-Red Group 32A.

*Flower.*—Form: cup-like with parallel sides, double. Diameter: approximately 5.5 to 6 cm. on average. Color (when opening begins): Upper surface: aureolin, Yellow Group 12A, and sometimes slightly edged with maize yellow, Yellow-Orange Group 21B. Under surface: aureolin, Yellow Group 12A, and sometimes slightly edged with Indian orange, Orange-Red Group 32A. Color (when blooming): Upper surface: aureolin, Yellow Group 12A, turning whitish on the outer petals. Under surface: aureolin, Yellow Group 12A, turning whitish on the outer petals. Color (at end of blooming): Upper surface: aureolin, Yellow Group 12A, turning whitish on the outer petals. Under surface: aureolin, Yellow Group 12A, turning whitish on the outer petals. Fragrance: very slight. Lasting quality: long lasting indoors or in the garden. Petal number: approximately 28 on average. Petal shape: oval. Petal texture: consistent. Petal drop: very good. Anthers: normal yellow edged with orange coloration. Stamen number: approximately 118 on average. Filaments: orange-yellow in coloration, and of irregular heights. Pistil number: approximately 73 on average. Stigmas: normal ochre. Styles: dark fuchsia in coloration, and tomentose near the base. Receptacle: medium green, smooth, wide and funnel-shaped.

Development:

*Vegetation.*—Very vigorous.

*Blooming.*—Abundant and continuous, in flushes.

*Resistance to diseases.*—Good.

I claim:

1. A new and distinct variety of miniature rose plant characterized by the following combination of characteristics:

(a) forms in abundance on a continuous basis attractive double long-lasting blossoms which are of a fairly stable aureolin yellow coloration,
(b) forms dark green glossy foliage,
(c) exhibits a very bushy and upright growth habit,
(d) is very quick to cycle,
(e) exhibits excellent garden performance and is well adapted to greenhouse forcing when grown in a container, and
(f) is not particularly affected by cryptogamic diseases;

substantially as herein shown and described.

* * * * *

MEICUPAG